United States Patent

Arhancet

[11] Patent Number: 5,907,071
[45] Date of Patent: May 25, 1999

[54] COMPOSITIONS AND METHODS FOR INHIBITING VINYL AROMATIC MONOMER POLYMERIZATION

[75] Inventor: Graciela B. Arhancet, Katy, Tex.

[73] Assignee: BetzDearborn Inc., Trevose, Pa.

[21] Appl. No.: 09/063,454

[22] Filed: Apr. 21, 1998

[51] Int. Cl.⁶ ........................... C07C 7/20
[52] U.S. Cl. .................... 585/5; 585/832; 585/950; 585/435; 208/48 AA; 203/9
[58] Field of Search ............... 585/4, 5, 832, 585/950, 435; 208/48 AA; 203/8, 9

[56] References Cited

U.S. PATENT DOCUMENTS

| | | | |
|---|---|---|---|
| 2,965,685 | 12/1960 | Campbell | 260/666.5 |
| 3,488,388 | 1/1970 | Altwicker et al. | 260/558 |
| 3,674,651 | 7/1972 | Otsuki et al. | 203/8 |
| 3,733,326 | 5/1973 | Murayama et al. | 260/290 |
| 3,747,988 | 7/1973 | Bailey | 203/8 |
| 4,105,506 | 8/1978 | Watson | 203/9 |
| 4,237,326 | 12/1980 | Fuga et al. | 585/4 |
| 4,376,678 | 3/1983 | Partos | 203/9 |
| 4,409,408 | 10/1983 | Miller | 585/4 |
| 4,466,905 | 8/1984 | Butler et al. | 252/403 |
| 4,670,131 | 6/1987 | Ferrell | 208/48 AA |
| 4,720,566 | 1/1988 | Martin | 558/306 |
| 4,774,374 | 9/1988 | Abruscato et al. | 585/24 |
| 4,885,413 | 12/1989 | Campbell et al. | 570/104 |
| 4,956,020 | 9/1990 | Nakajima | 134/22.19 |
| 5,254,760 | 10/1993 | Winter et al. | 585/5 |
| 5,282,957 | 2/1994 | Wright et al. | 208/48 AA |
| 5,426,257 | 6/1995 | Arhancet | 585/5 |
| 5,446,220 | 8/1995 | Arhancet | 585/5 |
| 5,489,718 | 2/1996 | Arhancet | 585/5 |
| 5,489,720 | 2/1996 | Arhancet | 585/5 |
| 5,510,547 | 4/1996 | Arhancet et al. | 585/5 |
| 5,545,782 | 8/1996 | Winter et al. | 585/5 |
| 5,545,786 | 8/1996 | Winter et al. | 585/435 |
| 5,583,247 | 12/1996 | Nesvadba et al. | 560/2 |

FOREIGN PATENT DOCUMENTS 163428  11/1974  Czech Rep. .
240297  10/1987  European Pat. Off. .

*Primary Examiner*—Bekir L. Yildirim
*Attorney, Agent, or Firm*—Philip H. VonNeida

[57] ABSTRACT

The polymerization of vinyl aromatic monomers such as styrene is inhibited by the addition of a composition of a stable hindered nitroxyl radical and an oxime compound.

9 Claims, No Drawings

COMPOSITIONS AND METHODS FOR INHIBITING VINYL AROMATIC MONOMER POLYMERIZATION

FIELD OF THE INVENTION

The present invention relates to compositions and methods for inhibiting the polymerization of vinyl aromatic monomer compounds.

BACKGROUND OF THE INVENTION

Common industrial methods for producing styrene typically include separation and purification processes such as distillation to remove unwanted impurities. Unfortunately, purification processes carried out at elevated temperatures result in an increased rate of undesired polymerization. Distillation is generally carried out under vacuum to minimize loss of monomer. The presence of oxygen, which is typically excluded from styrene distillation, will also promote polymerization of the monomer.

This polymerization results not only in loss of desired monomer end-product, but also in the uses of production efficiency caused by polymer formation and/or agglomeration of polymer on process equipment. Thermal polymerization, which typically occurs during distillation, of styrene monomer results in the formation of normal (i.e., linear) polymer. This resulting polystyrene polymer is characterized by its glassy and transparent appearance and its solubility in the styrene monomer and many organic solvents.

The compounds generally used commercially to inhibit polymerization of vinyl aromatic monomers are of the dinitrophenol family. For example, U.S. Pat. No. 4,105,506, Watson et al. teaches the use of 2,6-dinitro-p-cresol as a polymerization inhibitor for vinyl aromatic compounds. U.S. Pat. No. 4,466,905, Butler et al. teaches that a combination of 2,6-dinitro-p-cresol and p-phenylenediamine will inhibit polymerization in a distillation column when oxygen is present. U.S. Pat. No. 4,774,374, Abruscato et al. teaches compositions for inhibiting the polymerization of vinyl aromatic compounds. The composition is an oxygenated product of the reaction of N-aryl-N'-alkyl-p-phenylenediamine with oxygen. U.S. Pat. Nos. 5,426,257 and 5,489,718, Arhancet, teach methods and compositions for inhibiting the polymerization of vinyl aromatic monomers comprising an oxime compound and a hydroxylamine compound and/or a phenylenediamine.

U.S. Pat. No. 5,254,760, Winter et al. teaches compositions and processes for inhibiting vinyl aromatic compound polymerization. The processes comprise adding to the vinyl aromatic compounds during purification or distillation a mixture of a stable hindered nitroxyl compound and an aromatic nitro compound. U.S. Pat. No. 4,670,131, Ferrell, teaches methods for inhibiting fouling of hydrocarbons containing unsaturated compounds with a stable free radical. The stable free radical can be a nitroxide compound.

A variety of inhibitor compositions have been employed in styrene and other vinyl aromatic monomers to inhibit undesired polymerization. Agents that have been used include sulfur, p-benzoquinone, tert-butyl pyrocatechol, phenothiazine, and hindered phenols. However, many of these compounds present disadvantages such as high intoxicity, instability, explosive hazard at elevated temperature and insufficient efficacy under processing conditions (i.e., inhibitor requires oxygen to be effective). The present inventor has discovered a novel composition which acts to inhibit vinyl aromatic monomer polymerization while avoiding the problems of certain known inhibitors.

DETAILED DESCRIPTION OF THE INVENTION

The present invention relates to compositions and methods for inhibiting the polymerization of vinyl aromatic monomer compounds comprising adding to the monomers a combination of a stable hindered nitroxyl radical and an oxime compound.

The compositions of the present invention are effective at inhibiting polymerization of vinyl aromatic monomers under processing conditions. These processing conditions include but are not limited to preparation, purification, distillation and vacuum distillation processes. The compositions of the present invention are effective in both processes where oxygen is present and under oxygen-free conditions. The term "oxygen-free" is meant to define the substantially oxygen free conditions under which vinyl aromatic monomers, particularly styrene, are often processed. These conditions, exemplified by distillation and purification processes generally have less than 2 parts per million parts of oxygen present and preferably less than 1 part of oxygen per million parts styrene.

The vinyl aromatic monomers that are treated by the compositions of the present invention include but are not limited to styrene, bromostyrene, divinylbenzene, and α-methylstyrene. The compositions of the present invention are particularly efficacious at inhibiting the polymerization of styrene monomer.

The stable hindered nitroxyl radical generally has the formula

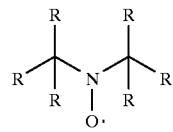

where R is a $C_1$ to $C_3$ alkyl group; or a cyclic compound having the formula:

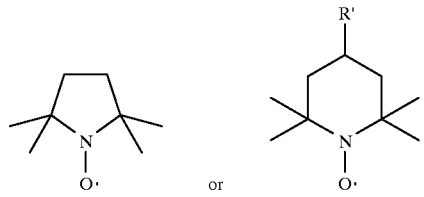

where R' is H, hydroxyl, =O, OCOR", R" is a C2 to C17 alkyl group; benzoate, phthalate, terephthalate, sebacate, succinate, and adipate.

The oxime compounds generally have the formula:

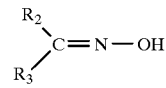

wherein $R_2$ and $R_3$ are the same or different and are hydrogen, alkyl, aryl, alkaryl, aralkyl, alkylhydroxyaryl or arylhydroxyalkyl groups having three to about twenty carbon atoms. Examples of these compounds include but are not limited salicylaldoxime and 5-nonylsalicylaldoxime.

The total amount of stable hindered nitroxyl radical and oxime compound used in the methods of the present invention is that amount which is sufficient to inhibit polymerization and will vary according to the conditions under which the vinyl aromatic monomer is being processed, and the temperature of the system. At higher processing temperatures and higher monomer contamination, larger amounts of the polymerization inhibiting composition are generally required.

Styrene, for example, is typically processed at temperatures between 95° and 125° C. The compositions of the present invention are effective at inhibiting the polymerization of styrene over this range of temperatures.

For purposes of the present invention, the term "effective inhibiting amount" is defined as that amount which is effective at inhibiting polymerization. Preferably the effective amount ranges from about 1 part to about 10,000 parts per million parts of monomer. More preferably, the effective amount ranges from about 1 part to about 1000 parts per million parts of monomer. Most preferably, the effective amount ranges from about 400 to about 600 parts per million parts of monomer.

The weight ratio of the stable hindered nitroxyl radical to oxime compound will generally range from about 9:1 to about 1:9 with a weight ratio of about 2:1 preferred. Most preferably the weight ratio is 1:1.

The compositions of the present invention can be added to the vinyl aromatic monomer by any conventional method at any point of the processing system, either as separate and individual ingredients or as a combination of ingredients.

The compositions of the present invention may be added to the vinyl aromatic monomer as either a dispersion or as a solution using a suitable liquid carrier or solvent. Any solvent that is compatible with the individual ingredients of the composition and the vinyl aromatic monomer to be treated may be employed.

Accordingly, it is possible to produce a more effective vinyl aromatic monomer polymerization inhibiting treatment than is obtained by the use of either compound by itself when measured at comparable treatment levels. This synergism or enhanced activity between components allows for the concentration of each of the components to be lowered and the total quantity of polymerization inhibitor required, particularly at higher temperatures, may be lowered while achieving a commensurate level of polymerization inhibition.

EXAMPLES

The invention will now be further described with reference to a number of specific examples which are to be regarded solely as illustrative, and not as restricting the scope of the invention.

5 mL of uninhibited styrene was placed in a test tube and the appropriate amount of treatment was added. The tube was capped with a rubber septum and argon was bubbled through the liquid at 10 mL/min for 3 minutes. The tubes utilized in Example 1 where then placed in an oil bath heated to 110° C. for 2 hours. The amount of polystyrene formed was determined by methanol precipitation. The results of this testing are presented in Table I.

TABLE I

Styrene Polymerization Test
Uninhibited Styrene at 110° C.

| Inhibitor | Dosage (ppm) | % Polymer Formed |
|---|---|---|
| Blank | — | 8.87 |
| SA | 200 | 8.43 |
| TEMPO | 200 | 0.76 |
| TEMPO/SA | 200/200 | 0.05 |
| TEMPO/SA | 134/66 | 0.77 |
| TEMPO/SA | 100/100 | 1.15 |
| TEMPO/SA | 66/134 | 2.04 |
| TEMPO | 100 | 1.77 |
| tAtBN | 200 | 0.29 |
| tAtBN/SA | 134/66 | 0.37 |
| tAtBN/SA | 100/100 | 0.48 |
| tAtBN/SA | 66/134 | 0.62 |
| OHTEMPO | 200 | 0.86 |
| OHTEMPO/SA | 200/200 | 0.25 |
| OHTEMPO/SA | 100/100 | 1.91 |
| OHTEMPO/NSA | 200/200 | 0.12 |

TEMPO is 2,2,6,6-tetramethyl-1-piperidinoxy, free radical
tAtBN is tert-amyl-tert-butyl aminoxyl, free radical
OHTEMPO is 4-hydroxy-2,2,6,6-tetramethyl-1-piperidinoxyl free radical
SA is salicylaldoxime
NSA is 5-nonylsalicylaldoxime As demonstrated in Table I, the salicylaldoxime compound was not very effective when employed by itself. A one to one ratio of TEMPO to SA at 400 ppm actives was very effective. Similar results were achieved when 400 ppm actives of OHTEMP and SA or NSA in a one to one ratio were used.

The procedure of Example 1 was repeated using an oil bath heated at 120° C. The results of Example 2 are reported in Table II.

TABLE II

Styrene Polymerization Test
Uninhibited Styrene at 120° C.

| Inhibitor | Dosage (ppm) | % Polymer Formed |
|---|---|---|
| Blank | — | 17.78 |
| TEMPO | 600 | 1.23 |
| TEMPO/SA | 400/200 | 0.68 |
| TEMPO/SA | 300/300 | 0.35 |
| TEMPO/SA | 200/400 | 2.70 |
| TEMPO | 300 | 3.49 |
| tAtBN | 600 | 0.44 |
| tAtBN/SA | 400/200 | 0.75 |
| tAtBN/SA | 300/300 | 0.53 |
| tAtBN/SA | 200/400 | 1.03 |
| tAtBN | 600 | 0.95 |

Table II reports a similar result in that one to one and two to one ratios of TEMPO to SA at 600 ppm actives were more effective than either 300 or 600 ppm of TEMPO used by itself.

For Example 3, uninhibited styrene (100 mL) was placed in a 250 mL three-necked flask fitted with a bubbler, a septa, and a condenser. 200 ppm of TEMPO and 200 ppm of SA were added and argon was bubbled through the solution at 10 mL/min for 10 minutes. While argon sparging continued, the flask was immersed in an oil bath heated at 110° C. 5.0 mL samples were taken every 30 minutes and the amount of polymer formed was determined by methanol precipitation. After heating for three hours, polymer content was 0.04%.

For Example 4, the procedure of Example 3 was followed except 300 ppm of TEMPO and 300 ppm of SA were immersed in an oil bath heated at 120° C. After heating for 2 hours, polymer content was 0.15%.

These results confirm the observations made in Tables I and II. 400 total ppm actives of TEMPO and SA in a one to one ratio resulted in the formation of little polymer. The same ratio at 600 ppm actives was also very effective.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what I claim is:

1. A method for inhibiting the polymerization of vinyl aromatic monomer comprising adding to said monomers about 400 to about 600 parts per million parts monomers of a composition comprising a stable hindered nitroxyl radical selected from the group consisting of 2,2,6,6-tetramethyl-1-piperidinoxy, free radical and 4-hydroxy-2,2,6,6-tetramethyl-1-piperidinoxy, free radical and an oxime compound selected from the group consisting of salicylaldoxime and 5-nonylsalicylaldoxime in a weight ratio of about 1:1.

2. The method as claimed in claim 1 wherein said vinyl aromatic monomer is styrene.

3. The method as claimed in claim 1 wherein said monomer is undergoing processing.

4. The method as claimed in claim 3 wherein said processing is at a temperature ranging from about 95° C. to about 125° C.

5. The method as claimed in claim 1 wherein oxygen is present in said vinyl aromatic monomer.

6. The method as claimed in claim 1 wherein said stable hindered nitroxyl radical is 2,2,6,6-tetramethyl-1-piperidinoxy, free radical and said oxime compound is salicylaldoxime.

7. The method as claimed in claim 6 wherein the weight ratio of stable hindered nitroxyl radical to oxime compound is about 1:1.

8. The method as claimed in claim 1 wherein said stable hindered nitroxyl radical is 4-hydroxy-2,2,6,6-tetramethyl-1-piperidinoxy, free radical and the oxime compound is selected from the group consisting of salicylaldoxime and 5-nonylsalicylaldoxime.

9. The method as claimed in claim 8 wherein the weight ratio of stable hindered nitroxyl radical to oxime compound is about 1:1.

* * * * *